United States Patent
Jeannotte et al.

(10) Patent No.: US 9,707,558 B2
(45) Date of Patent: Jul. 18, 2017

(54) FLUIDIC COUPLER ASSEMBLY WITH CONICAL FERRULE

(75) Inventors: Anthony C. Jeannotte, Foxborough, MA (US); John A. Leason, Taunton, MA (US); Charles T. Murphy, Norton, MA (US)

(73) Assignee: Waters Technologies Corporation, Milford, MA (US)

( * ) Notice: Subject to any disclaimer, the term of this patent is extended or adjusted under 35 U.S.C. 154(b) by 501 days.

(21) Appl. No.: 13/517,988

(22) PCT Filed: Dec. 20, 2010

(86) PCT No.: PCT/US2010/061208
§ 371 (c)(1),
(2), (4) Date: Aug. 30, 2012

(87) PCT Pub. No.: WO2011/079058
PCT Pub. Date: Jun. 30, 2011

(65) Prior Publication Data
US 2013/0043672 A1    Feb. 21, 2013

Related U.S. Application Data

(60) Provisional application No. 61/288,915, filed on Dec. 22, 2009.

(51) Int. Cl.
| | | |
|---|---|---|
| *F16L 3/127* | (2006.01) | |
| *B01L 3/00* | (2006.01) | |
| *G01N 21/03* | (2006.01) | |
| *G01N 21/05* | (2006.01) | |
| *G02B 6/36* | (2006.01) | |
| *G02B 6/38* | (2006.01) | |

(52) U.S. Cl.
CPC ......... *B01L 3/502715* (2013.01); *B01L 3/563* (2013.01); *G01N 21/0303* (2013.01);
(Continued)

(58) Field of Classification Search
CPC ....... B01L 3/502715; B01L 2200/0689; G01N 21/0303; G01N 21/05; G01N 2021/0307;
(Continued)

(56) References Cited

U.S. PATENT DOCUMENTS 2,182,811 A * 12/1939 Kocher ............................. 285/3
3,999,837 A    12/1976 Bowen et al.
(Continued)

FOREIGN PATENT DOCUMENTS

| FR | 2 296 862 A1 | 7/1976 |
|---|---|---|
| GB | 2 054 194 A | 2/1981 |

(Continued)

OTHER PUBLICATIONS

PCT Search Report for PCT/US2010/061208, international filing date Dec. 20, 2010, Form PCT/ISA/237 and PCT/ISA/210 date of mailing Feb. 17, 2011, 8 pages.
(Continued)

*Primary Examiner* — Gregory Binda
*Assistant Examiner* — Jay R Ripley
(74) *Attorney, Agent, or Firm* — Waters Technologies Corporation

(57) ABSTRACT

A fluidic coupler assembly (10) for use in a light-guided flow cell comprises a coupler body (12) having a sealing face (10a), a tubular insert such as an optical fiber (16) passing through a through bore (14) of the coupler body and through a ferrule (18) located adjacent the sealing face of the coupler body. A backing plug (20) holds the ferrule in position within the coupler body.

20 Claims, 3 Drawing Sheets

(52) U.S. Cl.
CPC ........... *G01N 21/05* (2013.01); *G02B 6/3624* (2013.01); *B01L 2200/0689* (2013.01); *G01N 2021/0307* (2013.01); *G01N 2021/0346* (2013.01); *G01N 2201/08* (2013.01); *G02B 6/3644* (2013.01); *G02B 6/3833* (2013.01); *G02B 6/3869* (2013.01); *Y10T 29/49826* (2015.01)

(58) Field of Classification Search
CPC ....... G01N 2021/0346; G01N 2201/08; G02B 6/3624; G02B 6/3644; G02B 6/3833; G02B 6/3869; Y10T 29/49826; F16L 3/127
USPC ....... 285/385, 354, 339, 341–343, 348, 353, 285/382.7; 96/106
See application file for complete search history.

(56) References Cited

U.S. PATENT DOCUMENTS

| | | | |
|---|---|---|---|
| 4,385,797 A * | 5/1983 | Dubois et al. | 385/94 |
| 5,110,431 A * | 5/1992 | Moring | 204/451 |
| 6,294,088 B1 | 9/2001 | Allington et al. | |
| 6,358,874 B1 | 3/2002 | Kobayashi et al. | |
| 6,542,231 B1 | 4/2003 | Garrett | |
| 7,207,727 B2 | 4/2007 | Tran et al. | |
| 7,316,777 B2 * | 1/2008 | Loy, Jr. | 210/198.2 |
| 7,516,989 B2 * | 4/2009 | Yoshida | 285/321 |
| 2004/0017981 A1 * | 1/2004 | Jovanovich et al. | 385/68 |
| 2006/0038402 A1 | 2/2006 | Norman et al. | |
| 2006/0179920 A1 | 8/2006 | Law et al. | |
| 2008/0038152 A1 | 2/2008 | Van Pelt | |

FOREIGN PATENT DOCUMENTS

| | | |
|---|---|---|
| WO | 2006/083597 A2 | 8/2006 |
| WO | 2009/088663 A1 | 7/2009 |

OTHER PUBLICATIONS

PCT Written Opinion for PCT/US2010/061208, international filing date Dec. 20, 2010, Form PCT/ISA/220 date of mailing Feb. 17, 2011, 5 pages.

Extended European Search Report for Application No. 10840022.7, issued Jan. 29, 2016 (9 pages).

* cited by examiner

FLUIDIC COUPLER ASSEMBLY WITH CONICAL FERRULE

RELATED APPLICATIONS

This application claims benefit of and is a continuation of to U.S. Provisional Application No. 61/288,915, filed Dec. 22, 2009. The contents of these applications are expressly incorporated herein by reference in its entirety.

FIELD OF THE INVENTION

This invention relates to a fluidic coupler assembly which accurately locates a tubular insert, such as an optical fibre and is particularly, although not exclusively, useful in a light guided flow cell of a chromatography system.

SUMMARY OF THE INVENTION

The coupler assembly of the present invention is less sensitive to manufacturing tolerances than previous constructions and permits more sealing force to be applied so that the assembly can withstand higher fluidic pressures. Moreover, the assembly aligns a tubular insert such as an optical fibre precisely on the axial centreline of a main body of the coupler. A fluidic seal is also created and maintained at a sealing surface of the coupler body.

One aspect of the present invention provides a fluidic coupler assembly for use in a light-guided flow cell which coupler comprises a coupler body having a sealing face, at least one tubular insert passing through a through bore of the coupler body and through a ferrule located adjacent the sealing face of the coupler body and means to hold the ferrule in position within the coupler body.

According to a feature of this aspect of the invention, the holding means may comprise a backing plug which abuts the ferrule within the coupler body remote from said sealing face and through which body the or each tubular bodyextends.

According to another feature of this aspect of the invention, the ferrule may have a frusto-conical nose which abuts a complementary frusto-conical portion of said through bore. Preferably, the through bore of the coupler body has a reduced diameter portion disposed between the frusto-conical portion of the coupler body and the sealing face.

According to a further feature of this aspect of the invention, the cone angle of the frusto-conical portion of the coupler body may be substantially larger than the complementary cone angle of the ferrule nose. Preferably, the cone angle of the frusto-conical portion of the coupler body is substantially 40° and the complementary cone angle of the ferrule nose is substantially 29°.

According to a still further feature of this aspect of the invention, the coupler body may be formed from a material which is harder and/or less compliant than that of the ferrule. Preferably, the backing plug is formed from material similar to that of the coupler body.

According to yet another feature of this aspect of the invention, the ferrule may be formed from a chemically inert polymer such as PEEK or fluropolymers including the various grades of Teflon® AF.

According to another feature of this aspect of the invention a plurality of coaxial tubular inserts may pass through the through bore of the coupler body and through the ferrule. In some constructions the or each tubular insert may be capillary, and optionally the or each tubular insert may be an optical fibre.

According to a still further feature of this aspect of the invention the coupler body may have a sealing face at each of its opposite axial ends, wherein at least one tubular insert passes through a through bore of the coupler body and through a ferrule located adjacent each of the opposed sealing faces of the coupler body and wherein said holding means comprises a backing plug within the couple body between, and providing a sealing face for, each of the ferrules.

Another aspect of the invention provides a method of assembling a fluidic coupler for use in a light guided flow cell, which method comprises threading a tubular insert through a through bore of a coupler body, threading a ferrule onto the tubular insert and inserting the ferrule into the through bore of the coupler body until complementary faces of the ferrule and the through bore are in abutment adjacent a sealing face of the coupler body, threading a backing plug onto the tubular insert and bringing the backing plug into abutment with the ferrule remote from said complementary faces, causing the backing plug to exert sufficient force on the ferrule that a portion of the ferrule is extruded from the sealing face of the coupler body.

According to a feature of this aspect of the invention, a further ferrule accommodated within a further coupler body may be threaded onto the or each tubular insert protruding from the backing plug remote from said sealing face and connecting together the coupler bodies so that a portion of the further ferrule is extruding from a sealing face of the further coupler body. According to a further feature of this aspect of the invention, the method may further comprise the step of trimming any excess tubular insert protruding from each sealing face and grinding, in each case the tubular insert, the extruded ferrule portion and the sealing face of each coupler body so that those respective components at each end of the assembly are flush.

DESCRIPTION OF THE DRAWINGS

Embodiments of the invention will now be described with reference to the accompanying drawings, in which.

DESCRIPTION OF THE INVENTION

Figure 1:
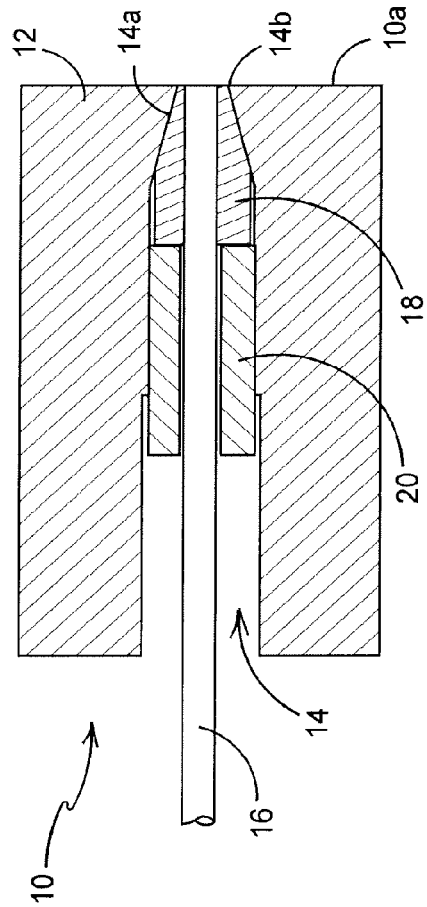
FIG. 1 is a vertical cross-section through a fluidic coupler assembly according to the invention.
Figure 2:
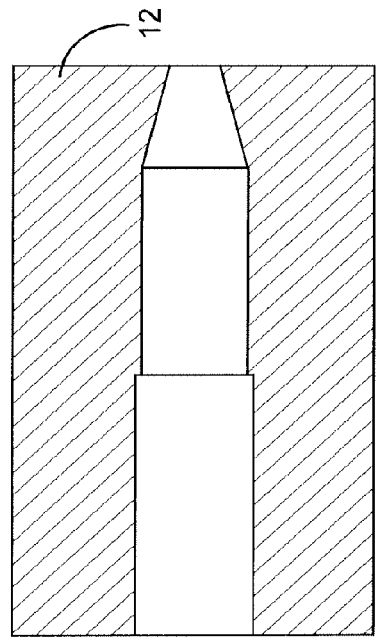
FIG. 2 is a vertical cross-section through a main coupler body of the assembly shown in FIG. 1.
Figure 2A:
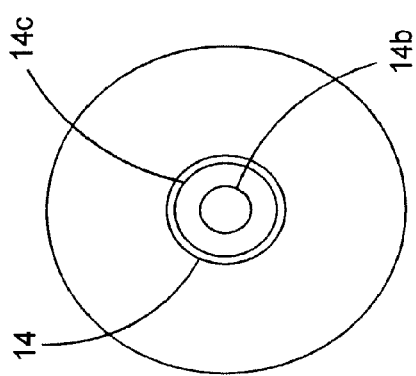
FIG.2a is an end view of the main coupler body of the assembly shown in FIG.2.
Figure 3:
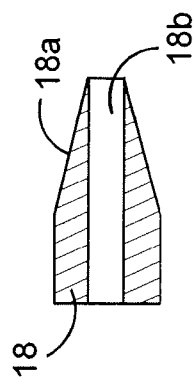
FIG. 3 is a vertical cross-section through a ferrule of the assembly.
Figure 4:
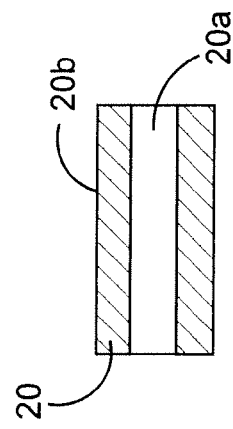
FIG. 4 is a vertical cross-section through a backing plug of the assembly.

Referring to the drawings, a coupler assembly 10 comprises a coupler body 12 which is machined from a suitable metal such as stainless steel but other materials are possible as long as the chosen material is harder or less compliant than the ferrule material. The assembly of this embodiment of the invention is described as incorporating an optic fibre 16 but other tubular inserts of various materials such as glass, metal and ceramics may be used. The coupler body has a generally cylindrical through bore 14 which at one end of the body has a frusto-conical portion 14a which terminates at a sealing face 10a of the coupler in a reduced diameter cylindrical portion 14b. This feature assures proper centering of the optical fibre 16. The coupler body incorporates a frusto-conical ferrule 18 which has a frusto-conical nose cone 18a which is complementary to the frusto-conical portion 14a of the through bore 14. The ferrule material must be softer or more compliant than the material of the coupler body 12. Such material may include but is not limited to chemically inert materials such as polyether ether ketone, known as "PEEK" or fluoropolymers, including the various grades of amorphous floroplastics, known as "Teflon® AF". The ferrule has a cylindrical through bore 18b which is slightly larger in diameter than the diameter of the optical fibre 16 which it is to receive. The cone angle machined into the coupler body is larger than the ferrule cone angle. In one arrangement the cone angle of the coupler body is 40° and the cone angle of the ferrule is 29° in order to concentrate deformation of the tip of the ferrule nose cone near the reduced diameter portion 14b of the coupler body.

The frusto-conical ferrule 18 will seal and accurately locate the optical fibre 16 in the coupler body 12. The ferrule is held in place within the coupler by a compression screw (not shown) or more preferably by means of a pressed-in cylindrical backing plug 20 having a through bore 20a. The backing plug has a slightly larger outside diameter than the inside diameter of the coupler body which creates an interference fit between the plug 20 and body 12 along the diameter 14. Depending upon the overall length of the body 12, it may be advantageous to make bore 14 slightly larger than diameter 20b of the backing plug but followed by the reduced diameter 14c which will now create the interference fit with plug 20. The diameter of the through bore 20a is sufficiently larger than the diameter of the optical fibre 16 so as to prevent damage to the optical fibre during assembly. The backing plug 20 is made from a material similar to the coupler body but sufficiently different in alloy composition as to reduce galling during assembly.

Figure 5:
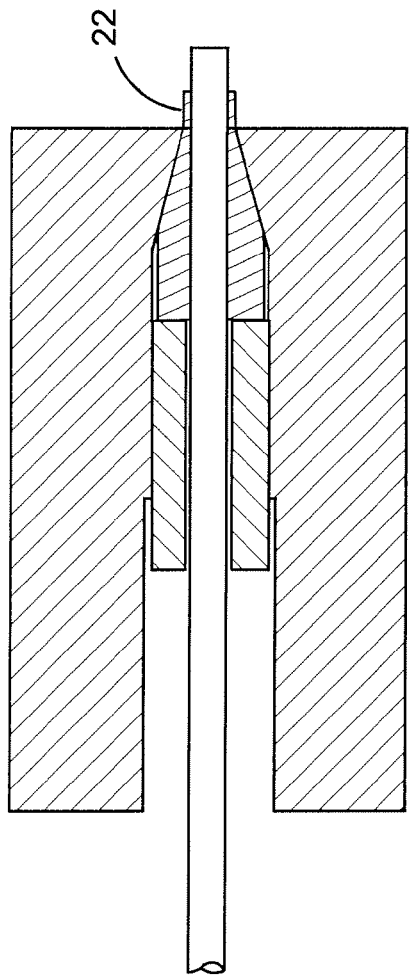
FIG. 5 is a vertical cross-section through the coupler assembly prior to grinding and polishing during the course of its manufacture.

In assembling the coupler, the optical fibre 16 is threaded through the through bore 14 of the coupler body 12 whereafter the ferrule 18 is threaded onto the optical fibre with its frusto-conical nose cone facing the frusto-conical end 14b of through bore 14a and the ferrule is then pushed into the coupler body. The backing plug 20 is then threaded onto the optical fibre 16 and is pressed into place within the through bore 14 or 14c as the situation requires, causing a small amount 22 (FIG. 5) of the ferrule to extrude through the reduced diameter portion 14b of the coupler bore at the coupler sealing face 10a, as shown in FIG. 5. Any excess fibre beyond the extruded portion of the ferrule is trimmed and the optical fibre, the ferrule and the sealing face are then ground and polished so that they are completely flush with the coupler sealing face. It can be appreciated that the final compressive loading around and along the fiber may be controlled by the extent to which the plug 20 is pressed into the bore 14 against the ferrule, the strength of the ferrule material and the specific tapered surfaces of both the ferrule, 18a, and body, 14a.

The foregoing method for securing an optical fiber within the body 12 may also be applied to other cylindrically-shaped objects; these could include glass, metal or polymeric capillaries or tubes, or wires. In the case of tubular inserts, it is oftentimes beneficial to install a sacrificial material such as a wax that can be easily removed after final processing, into the lumen of the tube prior to polishing. This provides a measure of mechanical support for the tube's inner diameter, minimizing edge chips or wall fractures.

Figure 6:
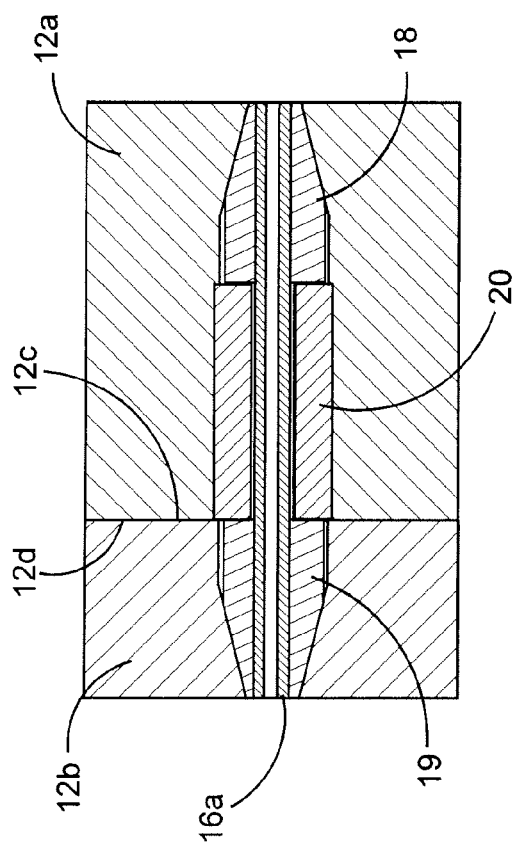
FIG. 6 is a vertical cross-section through a coupler assembly with a dual-ferruled captivation arrangement.

In an alternative embodiment of the invention, a double-ended seal may be effected using the captivation method described above. FIG. 6 depicts a two-part coupler comprising coupler bodies 12a and 12b, each having a frusto-conical portion for receiving a ferrule 18, 19 respectively. As shown, the complete assembly has already been polished at each end to remove by means of grinding and polishing the extruded ferrule material and, in this instance, a glass capillary 16a. The plug 20 is pressed flushe to surface 12c of coupler 12a by which point the desired extrusion of ferrule 18 has been realized. Ferrule 19 is then threaded onto tube 16a followed by coupler body 12a which is held in concentric relationship to 12a through well-known means such as dowel pins in part 12b engaging a hole and a slot in face 12c of 12b. Fastening means such as screws are then employed for joining body 12b to 12a so that surfaces 12d of part 12b and 12c of part 12a are flush. This joining process necessarily serves to extrude ferrule 19 beyond the exterior surface of 12b in like manner to that of pressing plug 20 against ferrule 18. The amount of ferrule compression may be controlled by well-known means such as the use of physical features such as stops in the coupler body. Axially aligning body part 12b to 12a may also be effected by fabricating the same bore in 12a used to contain plug 20 part way into 12b. Adjustments of the length of the plug 20 can accommodate a wide range of ferrule and coupler lengths 12a and 12b making it possible to fabricate complete couplers of lengths from a few millimetres to tens of centimeters. It is not always necessary to have an interference fit between the plug 20 and its receiving bore; in these cases there is a simultaneous loading and extrusion of each ferrule as the two coupler parts are brought and permanently fastened to one another.

Figure 6A:
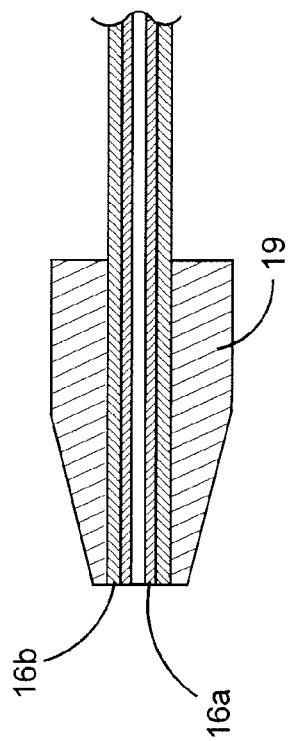
FIG. 6a is a vertical cross-section of a tubular insert showing an alternative structure having two coaxial tubes contained within a ferrule.

In yet a further embodiment of this assembly method, FIG. 6a illustrates an axial cylindrical structure that may consist of more than one tubular insert; for example, a glass tube 16a contained within a polymeric tube 16b. In many cases it is difficult if not impossible to find commercially available tubes having the requisite outside and inside diameters. This ferruling method permits some slight gap between the two coaxial tubes which is then eliminated during the ferrule extrusion process.

The invention claimed is:

1. A fluidic coupler assembly for use in a light-guided flow cell comprising:
 a coupler body having a first sealing face and a through bore, the through bore having a first region, a second region and a frusto-conical portion, the first region having a first diameter, the second region having a second diameter, wherein the second region is disposed between the first region and the frusto-conical portion and the second diameter is less than the first diameter;
 at least one tubular insert passing through the through bore of the coupler body and through a first ferrule located adjacent the first sealing face of the coupler body; and
 a backing plug abutting the ferrule within the through bore of the coupler body, the backing plug having an outside diameter sufficient to form an interference fit within the second region of the through bore of the coupler body such that the backing plug holds the first ferrule in position within the coupler body;
 wherein the at least one tubular insert extends though the backing plug;

wherein the at least one tubular insert and the first ferrule are flush with the first sealing face.

2. The fluidic coupler assembly of claim 1, wherein the first ferrule is formed from a chemically inert polymer such as polyether ether ketone or fluoropolymers including amorphous fluoroplastics.

3. The fluidic coupler assembly of claim 1, wherein the at least one tubular insert includes a plurality of coaxial tubular inserts passing through the through bore of the coupler body and through the first ferrule.

4. The fluidic coupler assembly of claim 1, wherein the at least one tubular insert is a capillary.

5. The fluidic coupler assembly of claim 1, wherein the at least one tubular insert is an optical fibre.

6. The fluidic coupler assembly of claim 1, wherein the coupler body is formed from a material which is harder and/or less compliant than that of the first ferrule.

7. The fluidic coupler assembly of claim 6, wherein the backing plug is formed from material sufficiently different in alloy composition from the coupler body to reduce galling during assembly with the coupler body.

8. The fluidic coupler assembly of claim 1, wherein the first ferrule has a frusto-conical nose which abuts the frusto-conical portion of said through bore.

9. The fluidic coupler assembly of claim 8, wherein a cone angle of the frusto-conical portion of the coupler body is substantially larger than a cone angle of the first ferrule nose.

10. The fluidic coupler assembly of claim 9, wherein the cone angle of the frusto-conical portion of the coupler body is substantially 40° and the cone angle of the first ferrule nose is substantially 29°.

11. A fluidic coupler assembly for use in a light-guided flow cell, comprising:
a coupler body having a first sealing face and a through bore, the through bore having a first region and a frusto-conical portion, the first region having a first diameter, wherein the frusto-conical portion is disposed between the first region and the first sealing face;
at least one tubular insert passing through the through bore of the coupler body and through a first ferrule located adjacent the first sealing face of the coupler body; and
a backing plug abutting the first ferrule within the through bore of the coupler body, the backing plug having an outside diameter sufficient to form an interference fit within the first region of the through bore of the coupler body such that the backing plug holds the first ferrule in position within the coupler body;
wherein the coupler body has a second sealing face at an opposite axial end to the first sealing face, wherein the at least one tubular insert passes through the through bore of the coupler body and through the first ferrule and a second ferrule, each ferrule located adjacent each of the opposed sealing faces of the coupler body, wherein the backing plug provides a sealing face for each of the ferrules;
wherein a first end of the at least one tubular insert and the first ferrule are flush with the first sealing face, and a second end of the at least one tubular insert and the second ferrule are flush with the second sealing face.

12. The fluidic coupler assembly of claim 11, wherein at least one of the first ferrule and the second ferrule is formed from a chemically inert polymer such as polyether ether ketone or fluoropolymers including amorphous fluoroplastics.

13. The fluidic coupler assembly of claim 11, wherein the at least one tubular insert includes a plurality of coaxial tubular inserts passing through the through bore of the coupler body, the first ferrule, and the second ferrule.

14. The fluidic coupler assembly of claim 11, wherein the at least one tubular insert is a capillary.

15. The fluidic coupler assembly of claim 11, wherein the at least one tubular insert is an optical fibre.

16. The fluidic coupler assembly of claim 11, wherein the coupler body is formed from a material which is harder and/or less compliant than that of at least one of the first ferrule and the second ferrule.

17. The fluidic coupler assembly of claim 16, wherein the backing plug is formed from material sufficiently different in alloy composition from the coupler body to reduce galling during assembly with the coupler body.

18. The fluidic coupler assembly of claim 11, wherein the first ferrule has a frusto-conical nose which abuts the frusto-conical portion of said through bore.

19. The fluidic coupler assembly of claim 18, wherein a cone angle of the frusto-conical portion of the coupler body is substantially larger than a cone angle of the first ferrule nose.

20. The fluidic coupler assembly of claim 19, wherein the cone angle of the frusto-conical portion of the coupler body is substantially 40° and the cone angle of the first ferrule nose is substantially 29°.

* * * * *